United States Patent [19]

Friedman

[11] Patent Number: 4,503,074

[45] Date of Patent: Mar. 5, 1985

[54] HALOGENATED GEMINAL DIESTERS

[75] Inventor: Arthur J. Friedman, Marlboro, N.J.

[73] Assignee: Merck & Co., Inc., Rahway, N.J.

[21] Appl. No.: 520,942

[22] Filed: Aug. 8, 1983

[51] Int. Cl.$^3$ ..................... A61K 31/225; C07C 69/38
[52] U.S. Cl. ................................... 514/547; 560/180; 560/181; 562/583
[58] Field of Search ............... 560/180, 181; 562/583; 424/313

[56] References Cited

U.S. PATENT DOCUMENTS

| | | | |
|---|---|---|---|
| 2,320,034 | 5/1943 | D'Ianni | 560/180 |
| 3,317,568 | 5/1967 | Wygant et al. | 562/596 X |
| 3,608,084 | 9/1971 | Matt | 260/465.7 |
| 3,833,731 | 9/1974 | Grier et al. | 424/304 |
| 3,873,597 | 3/1975 | Harmetz et al. | 260/465.7 |
| 3,877,922 | 4/1975 | Grier et al. | 71/67 |
| 4,328,363 | 5/1982 | Heiba et al. | 560/82 |

FOREIGN PATENT DOCUMENTS 1424943  2/1976  United Kingdom .

OTHER PUBLICATIONS

Chemical Abstracts, vol. 64, 12543d–12544a, (1966).
Chemical Abstracts, vol. 70, 67935x, (1969).
Gershon et al., J. Med. Chem., 20 (4) 606 (1977).
Motoyama et al., Ann. Sankyo Res. Lab. 23, 233–244 (1971).
Tanaha et al., Chem. Abstr. 84: 39698t (1976).

*Primary Examiner*—Natalie Trousof
*Assistant Examiner*—Vera C. Clarke
*Attorney, Agent, or Firm*—R. Brent Olson; Alice O. Robertson

[57] ABSTRACT

Certain new halogenated geminal diester compounds are described. The products are useful as broad spectrum antimicrobials.

5 Claims, No Drawings

HALOGENATED GEMINAL DIESTERS

DESCRIPTION OF THE INVENTION

The present invention is directed to certain halogenated geminal diester compounds represented by the formula:

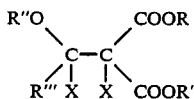

In this and succeeding formulas, R and R' are independently lower alkyl, R" is lower alkyl, R'" is hydrogen or lower alkyl, and X is halogen.

By "lower alkyl" is meant a radical having from 1 to about 4 carbon atoms. The halogen substituents may be chlorine or bromine.

The products of the present invention are colorless or light amber or yellow colored liquids soluble in organic solvents. The compounds are unstable at elevated temperatures and are susceptible to decomposition at elevated temperatures.

The compounds of the present invention are useful as broad-spectrum antimicrobial agents for the control of bacteria, yeast and fungi. The compounds are especially useful against certain genera of microorganisms against which many ester compounds which impart similar physical properties to the composition are ineffective. Thus, they are especially useful for the control of Aerobacter bacteria and Saccharomyces yeast genera. For the control of fungal organisms, the compounds are exceedingly useful, showing high degree of control over all genera normally considered undesirable and requiring control.

The compounds of the present invention may be prepared by reacting an appropriate halogen with an appropriate dialkyl alkoxyalkylenemalonate compound represented by the formula:

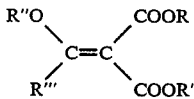

to produce the desired halogenated geminal diester compound of Formula I. The reactants may be brought together in an inert organic solvent. Suitable solvents for carrying out the reaction are hydrocarbons, ethers, esters, and preferably, halogenated lower alkanes such as methylene chloride, ethylene chloride, chloroform, carbon tetrachloride and the like. The exact amounts of the reactants are not critical, some of the desired product being obtained when any proportion of ingredients is employed; however, good results are obtained when employing substantially equal molar proportions of dialkyl alkoxyalkylenemalonate and halogen. The reaction may be carried out over a temperature range of from about $-15°$ to about $30°$ C. Cooling is almost always employed when the reactant halogen is chlorine. The temperature may be controlled by regulating the rate at which the reagents are combined and/or by employing external cooling. The reaction is rapid, generally instantaneous and is complete within a few minutes to an hour but is preferably allowed to continue for several hours or conveniently overnight to assure maximum formation of the desired product. After completion of the product formation, the solvent is removed from the reaction mixture by vaporization, preferably under reduced pressure, and the product recovered as residue. The product may be purified by chromatographic procedures since it is susceptible to decomposition on distillation. A useful method is passing the crude product through a silica gel column using a solvent such as diethyl ether.

The halogen reactant is preferably chlorine or bromine. It is generally employed as a preformed organic solvent solution. When the halogen is chlorine, the gaseous chlorine may be bubbled through the reaction medium, however, use in a solvent medium is preferred.

The dialkyl alkoxyalkylenemalonate starting materials are colorless liquids of low solubility in water and of high solubility in organic solvents. Some malonate compounds are available commercially. Others may be prepared as hereinafter described.

The dialkyl alkoxyalkylenemalonate starting material, Formula II, conveniently may be prepared from an appropriate malonic ester, orthoalkanoic ester and acetic anhydride in the presence of zinc chloride or other Lewis acid catalyst, in a manner similar to that described in J. Org. Chem. 11, 194 (1946). The reaction may be represented by the following equation:

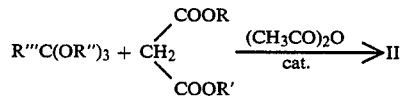

The reaction is usually carried out by thoroughly contacting, generally by mixing together and heating below the boiling temperature of the reactants for from several hours to overnight, an appropriate malonic ester, a slight molar excess of orthoalkanoic ester, and about two molar amounts of acetic anhydride in the presence of a catalyst whereupon a reaction takes place with the formation of dialkyl alkoxyalkylenemalonate in the reaction mixture. An additional amount of orthoalkanoic ester and acetic anhydride then are added, and the temperature of the reaction mixture increased and the pressure reduced somewhat to distill off low boiling by-products such as acetate ester and acetic acid, and to drive the reaction toward completion with the formation of the desired dialkyl alkoxyalkylenemalonate of Formula II. Thereafter, the mixture is fractionally distilled to recover purified alkoxyalkylenemalonate starting material.

The orthoalkanoic esters used in the foregoing preparation when a methyl or ethyl ester are generally available commercially. The higher esters may be prepared by a transesterification reaction employing an appropriate higher alcohol and methyl or ethyl orthoalkanoate. The reaction may be carried out in a manner similar to that described in J. Am. Chem. Soc. 74, 554 (1952) for the preparation of higher orthoformic esters from ethyl orthoformate. Alternatively, higher orthoformic esters may be prepared by the reaction of alcohol, hydrogen cyanide and hydrogen chloride as described in J. Org. Chem. 26, 1573 (1955). Another method for the preparation of orthoalkanoic esters is via the Williamson synthesis employing the appropriate sodium alkoxide and 1,1,1-trihaloalkane in a manner similar to that described in Organic Syntheses, volume 5, pp. 258-261, for the preparation of ethyl orthoformate from sodium ethoxide and chloroform.

Mixed esters of malonic acid may be prepared from the commercially available monoethyl ester monoacid chloride of malonic acid (carbethoxyacetyl chloride). The preparation may be carried out by adding malonyl chloride monoethyl ester in an inert solvent such as methylene chloride to a solution of the desired alkanol also in an inert solvent (in stoichiometric amounts) while the mixture is cooled in an ice bath and thereafter fractionally distilling to obtain the desired mixed ester starting material.

In a preferred method of carrying out the syntheses of the geminal diester compounds of Formula I, which may be named dialkyl α-halo-α-(1-halo-1-alkoxyalkyl)-malonates, a solution of halogen in methylene chloride is added dropwise with stirring at a temperature in the range of from about −15° C. to 30° C. to a solution of dialkyl alkoxyalkylenemalonate in methylene chloride and the stirring continued overnight. Following completion of the reaction, the product is separated and purified as previously described.

Certain dialkyl alkoxyalkylenemalonates as represented by the following structure:

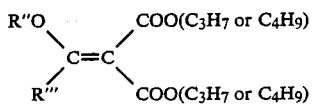

which may be formed by transesterification of the appropriate diethyl or dimethyl ester are novel and useful as intermediates, and constitute an aspect of the present invention. In carrying out the preparation of these higher dialkyl alkoxyalkylenemalonates, diethyl alkoxyalkylenemalonate, the appropriate propanol or butanol and an acid catalyst such as p-toluenesulfonic acid are mixed together and heated at reflux temperature for from a few minutes to about an hour, and thereafter fractionally distilled to obtain the desired dipropyl or dibutyl alkoxyalkylenemalonate intermediate.

The following examples illustrate the invention but are not to be construed as limiting.

EXAMPLE I Diehyl
α-Bromo-α-(1-bromo-1-ethoxymethyl)malonate

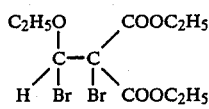

A solution of 4.00 grams (0.025 mole) of bromine in 75 milliliters of methylene chloride was added dropwise to a solution of 5.4 grams (0.025 mole) of diethyl ethoxymethylenemalonate in 75 milliliters of methylene chloride and the mixture stirred for 16 hours after which time the reaction mixture had become pale yellow in color with the formation of diethyl α-bromo-α-(1-bromo-1-ethoxymethyl)malonate (also named ethyl 2-carbethoxy-2,3-dibromo-3-ethoxypropionate) product. The product was purified by passing through a silica column with ethyl acetate to obtain a purified product as a colorless liquid. The product had elemental analyses as follows:

Calculated for $C_{10}H_{16}Br_2O_5$ (m.w. 376.05): Calc'd: C, 32.54; H, 4.29; Br, 42.50. Found: C, 31.94; H, 4.19; Br, 41.26.

EXAMPLE II
Di-n-butyl α-Bromo-α-(1-bromo-1-ethoxymethyl)malonate

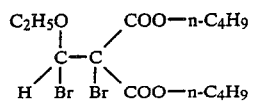

Preparation of di-n-butyl ethoxymethylenemalonate by transesterification

A mixture of 21.6 grams (0.10 mole) of diethyl ethoxymethylenemalonate, 14.8 grams (0.20 mole) of n-butanol and a catalytic amount (0.02 gram) of p-toluenesulfonic acid was heated to reflux with stirring for about 15 minutes whereupon a reaction started with the formation of dibutyl ethoxymethylenemalonate and ethanol in the reaction mixture. The reaction mixture was subjected to atmospheric distillation to remove the ethanol and to complete the formation of a dibutyl ethoxymethylenemalonate ester intermediate which remained as residue. The ester intermediate was distilled in vacuo to obtain a purified ester as a colorless oil, b.p. 143°–45° C./1.2 millimeters.

Preparation of di-n-butyl α-bromo-α-(1-bromo-1-ethoxy methyl)malonate

To a stirred solution of 13.6 grams (0.05 mole) of di-n-butyl ethoxymethylenemalonate in 50 milliliters of methylene chloride was added dropwise over a 10 minute period, a solution of 8.0 grams (0.05 mole) of bromine in 50 milliliters of methylene chloride. Stirring was continued for 18 hours after which the solvent was removed in vacuo to obtain as residue the desired di-n-butyl α-bromo-α-(1-bromo-1-ethoxymethyl)malonate Eas an orange yellow oil. The oil was chromatographed on silica with added ether as the mobile phase using a Waters Prep LC/System 500A liquid chromatograph. The ether then was removed from the eluate to recover 17.75 grams (82 percent yield) of purified product as a yellow oil. The product had analyses as follows:

Calculated for $C_{14}H_{24}Br_2O_5$ (m.w. 432.16):
Calc'd: C, 38.91; H, 5.60; Br, 36.98.
Found: C, 38.35; H, 5.98; Br, 35.82.

EXAMPLE III
Di-n-propyl α-Bromo-α-(1-bromo-1-ethoxyethyl)malonate

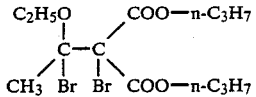

In reactions carried out in a manner similar to that described in Example II, a solution of 8.0 grams (0.05 mole) of bromine in 50 milliliters of methylene chloride is added to a stirred solution of 12.9 grams (0.05 mole) of di-n-propyl α-(1-ethoxyethylidene)malonate in 50 milliliters of methylene chloride. After completion of the addition, stirring is continued and the mixture allowed to stir overnight. Thereafter, the solvent is removed under reduced pressure to obtain as residue a di-n-propyl α-bromo-α-(1-bromo-1-ethoxyethyl)malonate product as an oil.

EXAMPLE IV

In reactions carried out in a manner similar to that described in the foregoing examples, the following compounds are prepared:

Dimethyl α-bromo-α-(ethoxymethylene)malonate from 8.7 grams (0.05 mole) of dimethyl methoxymethylenemalonate and 8.0 grams (0.05 mole) of bromine.

Dimethyl α-bromo-α-(1-bromo-1-isopropoxymethyl)malonate from 10.1 grams (0.05 mole) of dimethyl isopropoxymethylenemalonate and 8.0 grams (0.05 mole) of bromine.

Diethyl α-bromo-α-(1-bromo-1-n-butoxymethyl)malonate from 12.2 grams (0.05 mole) of diethyl n-butoxymethylenemalonate and 8.0 grams (0.05 mole) of bromine.

EXAMPLE V

In a reaction carried out in a similar manner, a solution of 3.5 grams (0.05 mole) of chlorine in 50 milliliters of methylene chloride is added to a cooled (dry ice bath) and stirred solution of diethyl ethoxymethylenemalonate in 50 milliliters of methylene chloride. The mixture is allowed to stir in the dry ice bath overnight. Thereafter, with continued stirring the mixture is allowed to warm up to room temperature to complete the reaction with the formation of a diethyl α-chloro-α-(1-chloro-1-ethoxymethyl)malonate product. The product has a molecular weight of 287.

EXAMPLE VI

In similar reactions the following compounds may be prepared:

Dimethyl α-chloro-α-(1-chloro-1-methoxymethyl)malonate.
Di-n-butyl α-chloro-α-(1-chloro-1-methoxymethyl)malonate.
Di-n-butyl α-chloro-α-(1-chloro-1-n-butoxymethyl)malonate.
Di-n-propyl α-chloro-α-(1-chloro-1-isopropoxymethyl)malonate.
Diethyl α-chloro-α-(1-chloro-1-ethoxypropyl)malonate.
Diethyl α-bromo-α-(1-bromo-1-ethoxy-n-butyl)malonate.
Diethyl α-chloro-α-(1-chloro-1-ethoxyethyl)malonate.
Diethyl α-bromo-α-(1-bromo-1-ethoxyamyl)malonate.
Methyl ethyl α-chloro-α-(1-chloro-1-ethoxymethyl)malonate.
Methyl ethyl α-bromo-α-(1-bromo-1-ethoxymethyl)malonate.
Ethyl isopropyl α-bromo-α-(1-bromo-1-ethoxymethyl)malonate.
Ethyl n-propyl α-bromo-α-(1-bromo-1-methoxy-n-butyl)malonate.
Ethyl-n-butyl α-bromo-α-(1-bromo-α-(1-bromo-1methoxymethyl)malonate.
Methyl ethyl α-bromo-α-(1-bromo-1-ethoxypropyl)malonate.
Methyl ethyl α-bromo-α-(1-bromo-1-ethoxy-n-butyl)malonate.
Ethyl isopropyl α-chloro-α-(1-chloro-1-isopropoxyethyl)malonate.
Methyl ethyl α-bromo-α-(1-bromo-1-methoxy-n-propyl)malonate.

The halogenated geminal diester products of the present invention are effective antimicrobial agents and are adapted to be employed for the control of bacterial and fungal organisms in numerous applications particularly in aqueous compositions which need to be preserved and in aqueous industrial systems requiring antimicrobial control. The usefulness of the compounds may be illustrated by the following example:

EXAMPLE

The technique employed to determine antimicrobial spectrum is as follows:

A stock solution of the compound to be tested for antimicrobial activity is prepared in 25 percent methanol. Dilutions of the stock solution are made into Sabouraud Maltose Agar and the agar poured into sterile petri dishes. After hardening, the plates are streaked with an aqueous suspension of the test organism. The inoculated plates are incubated at about 30° C. and readings made after 24–48 hours incubation for the bacteria and 4–5 days incubation for the fungi. The lowest concentration that inhibits microbial growth is recorded as minimum inhibitory concentration.

The results obtained with diethyl α-bromo-α-(1-bromo-1-ethoxymethyl)malonate (also identifiable as ethyl 2-carbethoxy-2, 3-dibromo-3-ethoxypropionate) (Compound A) and with di-n-butyl α-bromo-α-(1-bromo-1-ethoxymethyl)malonate (Compound B) when tested at the following concentrations 10, 50, 100, 200, 400, 750 and 1000 ppm showed the minimum inhibitory concentration to be as follows:

|  | Minimum Inhibitory Concentration (ppm) | |
|---|---|---|
|  | Compound A | Compound B |
| *Aerobacter aerogenes* | 10/50 | 100/200 |
| *Pseudomonas aeruginosa* | 200 | 200/500 |
| *Saccharomyces cerevisiae* | 10/50 | 50 |
| *Aspergillus niger* | 10/50 | 50 |
| *Pullularia pullulans* | 10/50 | 50 |
| *Penecillium funiculosum* | 10/50 | 50 |
| *Alternaria brassicicola* | 10/50 | 50 |

In employing the geminal diesters of the present invention for antimicrobial control, antimicrobial compositions containing said esters may be prepared in a liquid, solid or aerosol inert carrier to be applied to the substrate or area where antimicrobial control is desired. Such compositions may contain the geminal diester in an amount of from about 0.1 percent to 10 percent by weight, or more if a concentrate composition. Inert carriers include liquids such as petroleum distillates, kerosene, benzene, toluene, and the like, and finely divided solids, such as surface active agents, clays, diatomaceous earth, bentonite, mahogany soaps, talc, attapulgite and the like. The compositions may be diluted or employed without modification to provide concentration in the substrate or area to be controlled of from 10 parts per million to 10,000 parts per million or more, depending on the organism and substrate.

What is claimed is:

1. A halogenated geminal diester compound represented by the formula

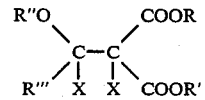

wherein

R, R' and R" are independently a lower alkyl group,
R'" is H or lower alkyl, and
X is chlorine or bromine.

2. A compound according to claim 1 which is diethyl α-bromo-α-(1-bromo-1-ethoxymethyl)malonate.

3. A compound according to claim 1 which is di-n-butyl α-bromo-α-(1-bromo-1-ethoxymethyl)malonate.

4. A composition for the control of bacteria, fungi and yeast comprising an inert carrier and an anti-bacteria, fungi and yeast effective amount of a compound of claim 1.

5. A method for inhibiting bacteria, fungi and yeast growth which comprises applying thereto an anti-bacteria, fungi and yeast effective amount of a compound of claim 1.

* * * * *